United States Patent
Kaiser et al.

(10) Patent No.: US 9,488,634 B2
(45) Date of Patent: Nov. 8, 2016

(54) FLOWABLE STOCK SAMPLING APPARATUS

(71) Applicant: Georgia-Pacific Consumer Products LP, Atlanta, GA (US)

(72) Inventors: Shawn M. Kaiser, Baton Rouge, LA (US); Glenn B. Duke, Gulfport, MS (US); Aaron K. McKinney, Addis, LA (US); Jeffrey A. Lee, Neenah, WI (US)

(73) Assignee: Georgia-Pacific Consumer Products LP, Atlanta, GA (US)

( * ) Notice: Subject to any disclaimer, the term of this patent is extended or adjusted under 35 U.S.C. 154(b) by 303 days.

(21) Appl. No.: 14/179,682

(22) Filed: Feb. 13, 2014

(65) Prior Publication Data

US 2014/0261886 A1 Sep. 18, 2014

Related U.S. Application Data

(60) Provisional application No. 61/770,039, filed on Feb. 27, 2013.

(51) Int. Cl.
*B65B 3/04* (2006.01)
*G01N 33/34* (2006.01)
*F16K 31/50* (2006.01)
*F16K 3/24* (2006.01)
*G01N 1/20* (2006.01)

(52) U.S. Cl.
CPC ............ *G01N 33/343* (2013.01); *F16K 3/246* (2013.01); *F16K 31/50* (2013.01); *G01N 2001/2071* (2013.01)

(58) Field of Classification Search
CPC ..................... G01N 33/343; G01N 2001/205; G01N 2001/2071; F16K 31/50
See application file for complete search history.

(56) References Cited

U.S. PATENT DOCUMENTS

| | | | |
|---|---|---|---|
| 2,446,587 A | 8/1948 | Henry | |
| 2,746,297 A | 5/1956 | Martin | |
| 3,490,736 A * | 1/1970 | Snyder | F16K 27/02 137/375 |
| 3,683,978 A | 8/1972 | Jones et al. | |
| 3,746,301 A * | 7/1973 | Budzich | F16B 21/20 188/67 |
| 4,114,427 A | 9/1978 | Iguchi et al. | |
| 4,118,987 A | 10/1978 | Zeh | |
| 4,252,021 A * | 2/1981 | Drushel | G01N 1/10 137/614 |
| 4,409,853 A | 10/1983 | Chase et al. | |
| 4,620,451 A | 11/1986 | Malmgren | |
| 4,864,877 A | 9/1989 | Ortiz et al. | |
| 4,887,472 A | 12/1989 | Jansen | |
| 4,949,858 A * | 8/1990 | Sheridan | B01L 3/508 215/293 |
| 4,974,456 A * | 12/1990 | Ortiz | G01N 1/10 141/59 |
| 5,265,483 A * | 11/1993 | Farrell | G01N 1/2035 422/534 |
| 5,370,005 A * | 12/1994 | Fjerdingstad | G01N 1/2035 73/863.71 |
| 5,431,067 A | 7/1995 | Anderson et al. | |

(Continued)

*Primary Examiner* — Jason K Niesz
(74) *Attorney, Agent, or Firm* — Laura L. Bozek

(57) ABSTRACT

A combination includes a container and a coupling configured to receive the container. The coupling has a unitary body having a first side and an opposing second side, the first side comprising a first orifice and a second orifice, the second side comprising a third orifice. The first orifice is disposed in flow-through communication with the third orifice from the first side to the second side, and the third orifice is disposed in flow-through communication with the second orifice from the second side to the first side. A first flow path through the first orifice is disposed parallel with a second flow path through the third orifice, and a third flow path through the third orifice is disposed parallel with a fourth flow path through the second orifice.

18 Claims, 7 Drawing Sheets

(56) References Cited

U.S. PATENT DOCUMENTS

| | | |
|---|---|---|
| 5,575,317 A | 11/1996 | Behnke et al. |
| 5,594,182 A | 1/1997 | Jansen |
| 5,673,737 A | 10/1997 | Behnke et al. |
| 5,970,805 A | 10/1999 | Foody et al. |
| 6,105,441 A | 8/2000 | Conner et al. |

* cited by examiner

FLOWABLE STOCK SAMPLING APPARATUS

CROSS REFERENCE TO RELATED APPLICATION

This application is based on U.S. Provisional Patent Application No. 61/770,039, filed Feb. 27, 2013, which is incorporated herein by reference in its entirety.

BACKGROUND OF THE INVENTION

The present disclosure relates generally to a sampling apparatus for use with flowable stock, and particularly to a sampling apparatus for use with cellulose pulp fiber in an aqueous solution in a pressurized system.

A problem encountered in connection with the collection and consistency control of samples of an aqueous solution of cellulose pulp fiber from a pressurized system is the waste and spillage of the material being sampled.

A problem encountered in connection with the collection and consistency control of samples of a viscous aqueous solution of cellulose pulp fiber from a pressurized system is clogging of the viscous pulp in the collection system and/or delivery system leading up to the collection system.

U.S. Pat. No. 4,620,451 discloses a cellulose pulp sampling and cleaning device having a wash chamber for washing the product to be sampled. A collection of valves, orifices, and conduits with bends provide flow control through a complex arrangement of non-linear flow paths.

U.S. Pat. No. 5,370,005 discloses a sampling assembly for taking a representative fluid sample from a pressurized fluid system. A pressure chamber houses a sampling container that receives a fluid sample from a manifold coupled to the pressurized system. A collection of valves, orifices, and flow passages with bends provide flow control through a complex arrangement of non-linear flow paths between the manifold and the pressure chamber.

U.S. Pat. No. 5,575,317 discloses a sample tap apparatus with a pressurized cap for taking fluid samples from a pressurized system. Removal of the cap enables a sample bottle to be attached to the base of the tap apparatus. A helical spring attached to a fill tube within the base is used to steady the mouth of the sample bottle as it is filled by the fill tube. A shut off valve can be used to stop the flow of sample before it spills out of the sample bottle between the coils of the helical spring.

While existing fluid sampling apparatus may be suitable for their intended purpose, there remains a need in the art for a sampling apparatus that provides for ease of filling a sample bottle with minimal flow restriction to avoid sample clogging and sample inhomogeneity, and that provides for a controlled discharge upon filling of the sample bottle.

This background information is provided to reveal information believed by the applicant to be of possible relevance to the present invention. No admission is necessarily intended, nor should be construed, that any of the preceding information constitutes prior art against the present invention.

BRIEF DESCRIPTION OF THE INVENTION

An embodiment of the invention includes a combination having a container and a coupling configured to receive the container. The coupling has a unitary body having a first side and an opposing second side, the first side comprising a first orifice and a second orifice, the second side comprising a third orifice. The first orifice is disposed in flow-through communication with the third orifice from the first side to the second side, and the third orifice is disposed in flow-through communication with the second orifice from the second side to the first side. A first flow path through the first orifice is disposed parallel with a second flow path through the third orifice, and a third flow path through the third orifice is disposed parallel with a fourth flow path through the second orifice.

Another embodiment of the invention includes a coupling having a unitary body having a first side and an opposing second side, the first side having a first orifice and a second orifice, the second side having a third orifice. The first orifice is disposed in flow-through communication with the third orifice from the first side to the second side, and the third orifice is disposed in flow-through communication with the second orifice from the second side to the first side. A first flow path through the first orifice is disposed parallel with a second flow path through the third orifice, and a third flow path through the third orifice is disposed parallel with a fourth flow path through the second orifice.

Another embodiment of the invention includes a combination of a shut off valve and a coupling configured to receive the shut off valve. The coupling includes a unitary body having a first side and an opposing second side, the first side having a first orifice and a second orifice, the second side having a third orifice. The first orifice is disposed in flow-through communication with the third orifice from the first side to the second side, and the third orifice is disposed in flow-through communication with the second orifice from the second side to the first side. A first flow path through the first orifice is disposed parallel with a second flow path through the third orifice, and a third flow path through the third orifice is disposed parallel with a fourth flow path through the second orifice.

Another embodiment of the invention includes a combination of a shut off valve, a container, and a coupling configured to receive both the shut off valve and the container. The coupling includes a unitary body having a first side and an opposing second side, the first side having a first orifice and a second orifice, the second side having a third orifice. The first orifice is disposed in flow-through communication with the third orifice from the first side to the second side, and the third orifice is disposed in flow-through communication with the second orifice from the second side to the first side. A first flow path through the first orifice is disposed parallel with a second flow path through the third orifice, and a third flow path through the third orifice is disposed parallel with a fourth flow path through the second orifice.

BRIEF DESCRIPTION OF THE DRAWINGS

Referring to the non-limiting drawings wherein like elements are numbered alike in the accompanying Figures.

DETAILED DESCRIPTION OF THE INVENTION

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

An embodiment of the invention, as shown and described by the various figures and accompanying text, provides a sampling apparatus for use with flowable stock, such as an aqueous solution of tissue paper, for example. More particularly, the sampling apparatus includes a sample container, such as a bottle, that is threadably coupled to a sample coupling. The sample coupling is a unitary body having an inlet orifice and an outlet orifice on a first side, and a sampling orifice on a second opposing side. As used herein, the term unitary body means a one-piece body having no parts that can be completely separated from the body during normal operation, maintenance or disassembly, having no parts that can be completely separated from the body without destroying some portion of the body, and containing no parts that are not integrally formed, where the term integrally formed means formed with material common to the rest of the body, such as a body produced from a machined single block of material or a forging metal-working process, for example.

The inlet and outlet orifices overlap the sampling orifice to define inlet and outlet flow paths having a straight line of entry and exit into and out of the sample bottle, thereby avoiding bends or corners in the flow path that could potentially clog and alter the homogeneity of the sample being taken. While an embodiment described herein depicts an example coupling that can be formed from a machining and turning operation, it will be appreciated that the disclosed invention is not limited to a particular method of manufacturing and is also contemplated to encompass other forms of manufacturing, such as forging, for example.

Figure 1:
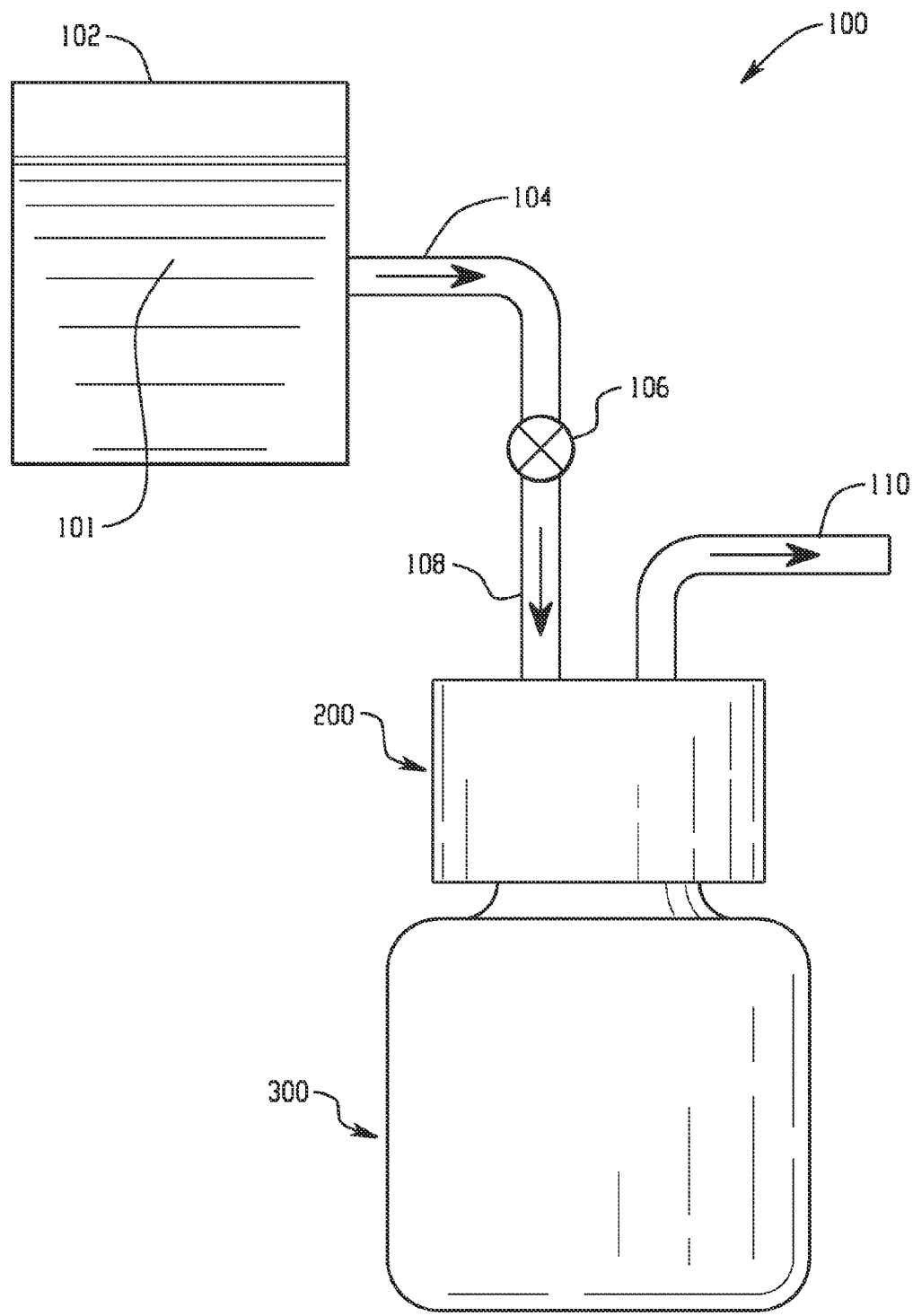
FIG. 1 depicts in block diagram form a system having a coupling and a sample container in accordance with an embodiment of the invention.

FIG. 1 depicts in block diagram form a system 100 that includes a pressurized fluid source 102, a sampling conduit 104, a shut off valve 106, an inlet conduit 108, a coupling 200, a sample container 300, and an outlet conduit 110. In an embodiment, the fluid in the pressurized fluid source 102 contains an aqueous solution of fibrous cellulosic materials that may be derived from natural sources, such as wood pulp fibers, as well as other fibrous material characterized by having hydroxyl groups attached to a polymer backbone. This fibrous material may include glass fibers and synthetic fibers modified with hydroxyl groups. Examples of sheet products that may be made using such aqueous solution of fibrous cellulosic materials include, but are not limited to, wipers, napkins, tissues, rolls, towels or other fibrous, film, polymer, or filamentary products. Hereinafter, the aforementioned aqueous solution of fibrous cellulosic materials will be referred to as flowable stock 101 (also herein referred to as viscous pulp). During a sampling procedure, flowable stock. 101 passes from the pressurized fluid source 102 to the sample container 300 via the sampling conduit 104 and the inlet conduit 108 when the shut off valve 106 is opened. When the sample container 300 is full, the flowable stock 101 is discharged via the outlet conduit 110. In an embodiment, the discharge is further processed by a process sewer.

Figure 2A:
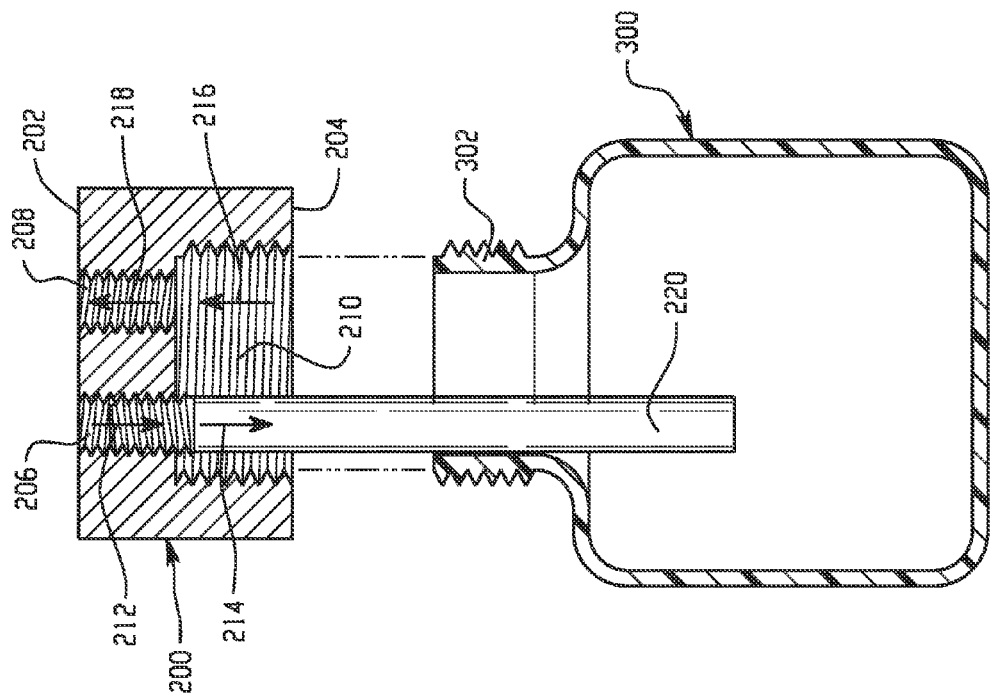
FIG. 2A depicts a cross section view of an exploded assembly of the coupling and sample container depicted in the system of FIG. 1, in accordance with an embodiment of the invention.
Figure 5:
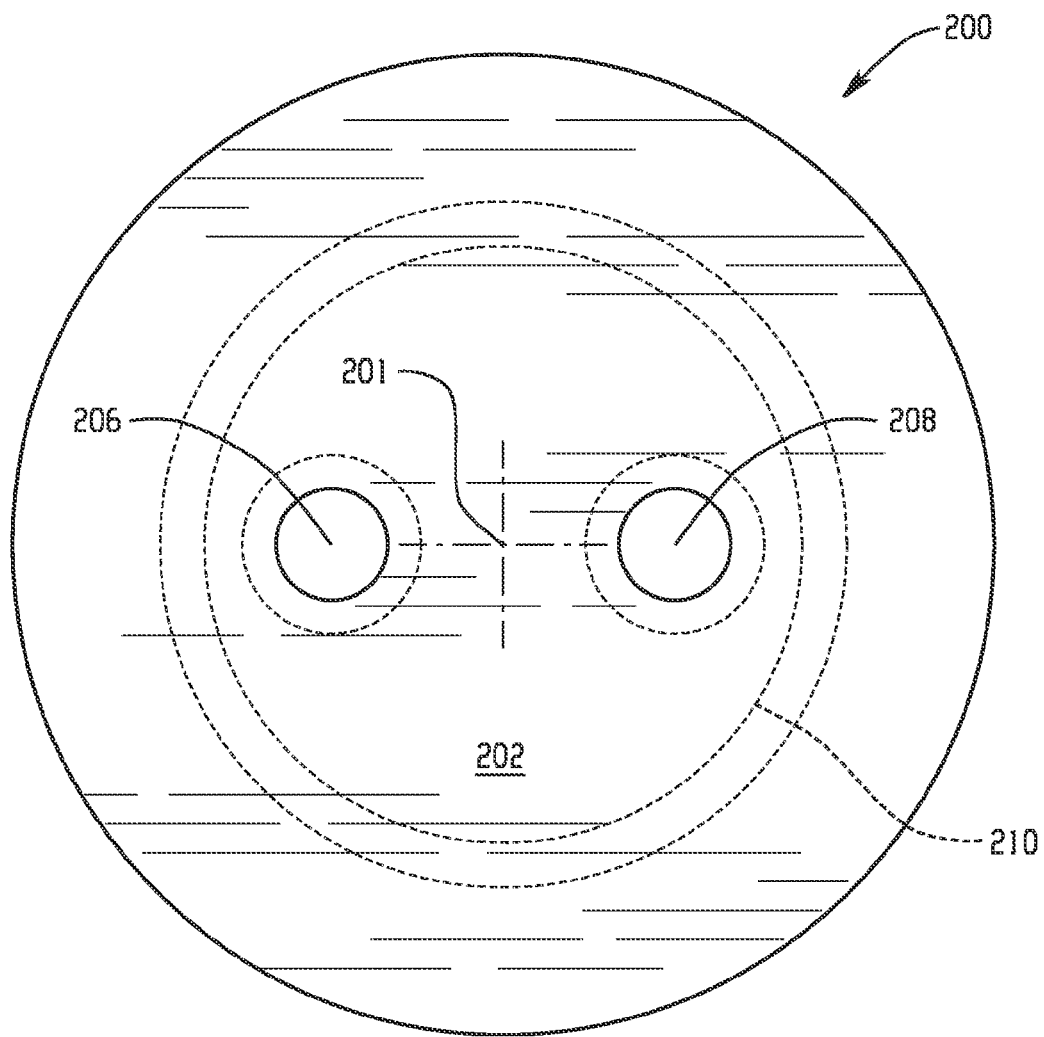
FIG. 5 depicts a top-down plan view of the coupling of FIGS. 2A, 3 and 4, in accordance with an embodiment of the invention.

FIG. 2A depicts in cross section view an exploded assembly of the coupling 200 and the sample container 300, where the cross section plane is a plane that contains a central axis of the coupling 200 and sample container 300. The central axis 201 of coupling 200 is depicted in FIG. 5. In an embodiment, the coupling 200 is formed from a unitary piece of material, such as aluminum for example, to form a unitary body (herein referred to by reference numeral 200) having no material seams that is, seamless continuity) from a first side 202 to a second opposing side 204 of the coupling 200. The coupling 200 includes a first orifice 206 and a second orifice 208 on the first side 202, and a third orifice 210 on the second side 204. In an embodiment, the first and second orifices 206, 208 are circularly drilled orifices having internal NPT (National Pipe Thread) tapered threads, and the third orifice 210 is a circularly drilled orifice having standard internal non-tapered threads. In an embodiment, the first orifice 206 and the second orifice 208 each overlap the third orifice 210 (depicted in FIG. 2A and also in FIG. 3, which will be discussed further below), such that the first orifice 206 is in flow-through communication with the third orifice 210 from the first side 202 to the second side 204, and the third orifice 210 is in flow-through communication with the second orifice 208 from the second side 204 to the first side 202. A first flow path 212 that passes through the first orifice 206 is disposed parallel with a second flow path 214 that passes through the third orifice 210, and a third flow path 216 that passes in a reverse direction through the third orifice 210 is disposed parallel with a fourth flow path 218 through the second orifice 208. During a sampling procedure, the flowable stock 101 enters the sample container 300 via the first and third orifices 206, 210, traversing, for example, the first and second flow paths 212, 214, and exits the sampler container 300 via the third and second orifices 210, 208, traversing, for example, the third and fourth flow paths 216, 218. In an embodiment, the sample container 300 is a bottle made from clear or semi-transparent plastic, such as thermoplastic for example, thereby enabling an operator to see when the sample container 300 is full enough for providing a sufficient sample size of the flowable stock 101. In an embodiment, the sample container 300 has a neck 302 with molded-in external threads configured to threadably engage with the internal threads of the third orifice 210. From the foregoing it will be appreciated that the coupling 200 is configured to directly threadably receive the sample container 300.

With reference still to FIG. 2A, it will be appreciated that an embodiment of the coupling 200 includes a variety of particular flow path arrangements. For example, an embodiment of the coupling 200 includes an arrangement where the first flow path 212 through the first orifice 206 is disposed parallel with the fourth flow path 218 through the second orifice 208. Another embodiment of the coupling 200 includes an arrangement where the first flow path 212 through the first orifice 206 is disposed in a straight line arrangement with the second flow path 214 through the third orifice 210, and the third flow path 216 through the third orifice 210 is disposed in a straight line arrangement with the fourth flow path 218 through the second orifice 208. Another embodiment of the coupling 200 includes an arrangement where the first flow path 212 through the first orifice 206 adjoins the second flow path 214 through the third orifice 210, and the third flow path 216 through the third orifice 210 adjoins the fourth flow path 218 through the second orifice 208. More particularly, an embodiment of the coupling 200 includes an arrangement where the first flow path 212 through the first orifice 206 adjoins the second flow path 214 through the third orifice 210 in a continuous uninterrupted manner, and the third flow path 216 through the third orifice 210 adjoins the fourth flow path 218 through the second orifice 208 in a continuous uninterrupted manner.

Figure 2B:
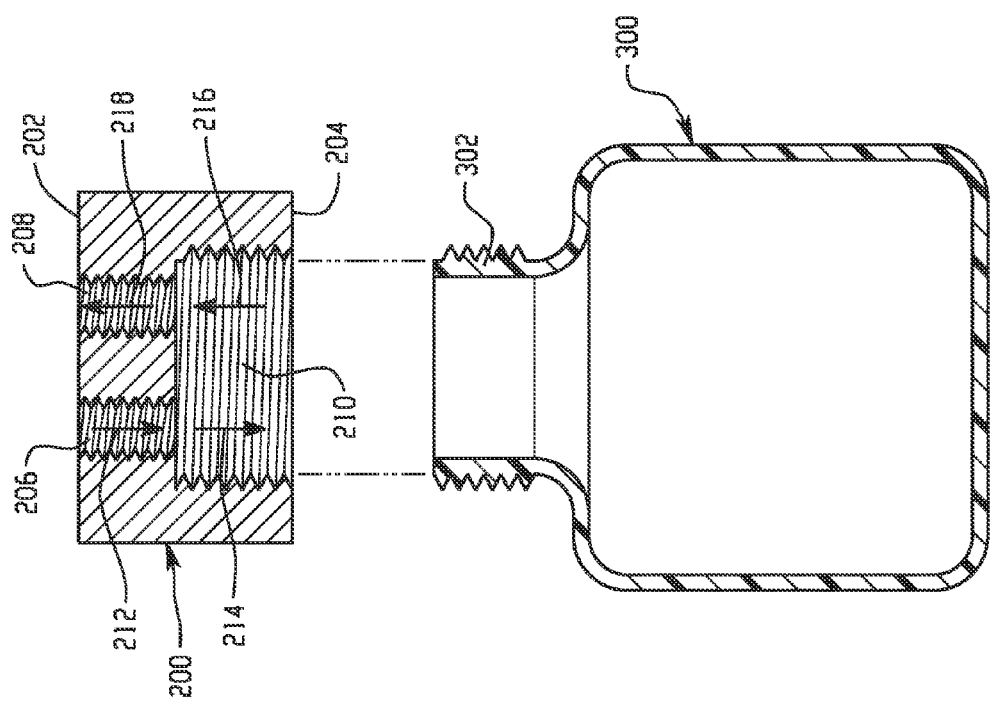
FIG. 2B depicts the cross section view of FIG. 2A with a dip tube included, in accordance with an embodiment of the invention.

FIG. 2B depicts in cross section view of the exploded assembly of the coupling 200 and the sample container 300 of FIG. 2A, but with the inclusion of a dip tube 220 threadably coupled to the first orifice 206, the dip tube 220 serving to direct the viscous pulp 101 (FIG. 1) toward the bottom of the sample container 300 to avoid plugging at the neck 302 or at the interface where the neck 302 attaches to the third orifice 210 of the coupling 200. In an embodiment, the dip tube 220 extends at least half way down into the sample container 300 such that the bottom end of the dip tube 220 is disposed closer to the bottom of the sample container 300 than to the top.

Figure 3:
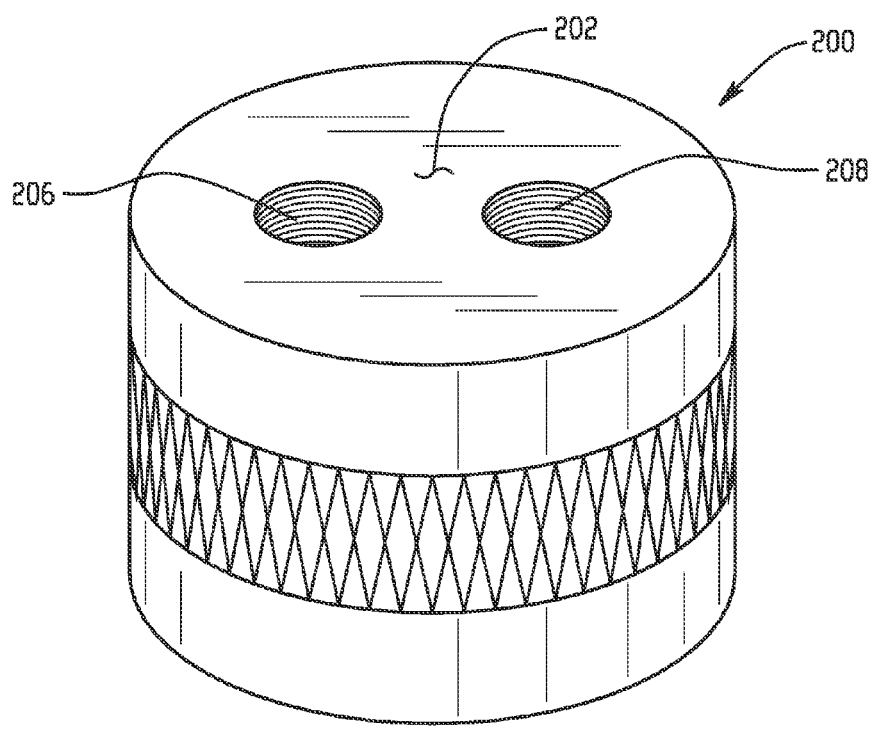
FIG. 3 depicts a top perspective view of the coupling of FIG. 2A, in accordance with an embodiment of the invention.
Figure 4:
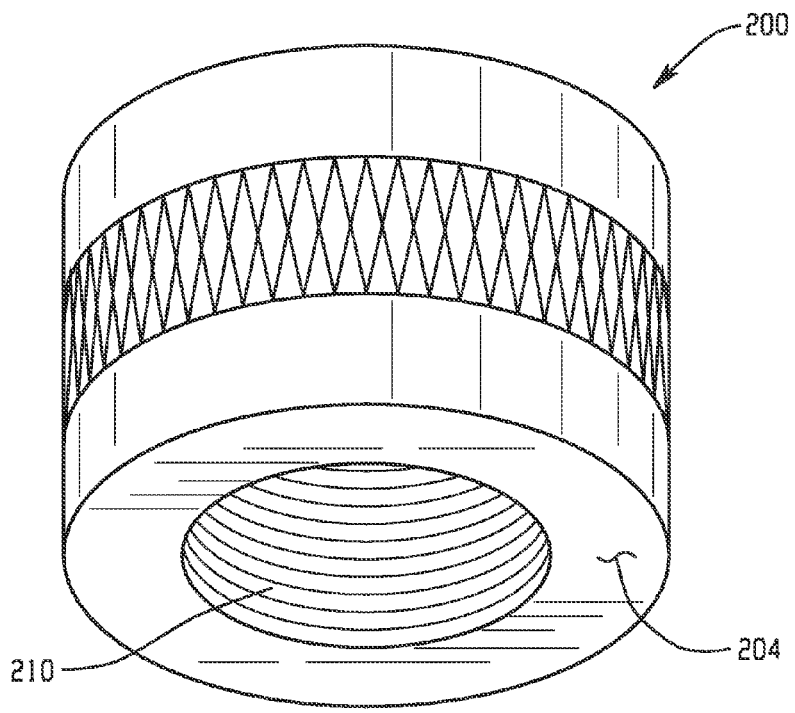
FIG. 4 depicts a bottom perspective view of the coupling of FIGS. 2A and 3, in accordance with an embodiment of the invention.

FIGS. 3 and 4 depict, respectively, a top perspective view and a bottom perspective view of an embodiment of the coupling 200 consistent with the coupling 200 depicted in FIG. 2A, and FIG. 5 depicts a top-down plan view of an embodiment of the coupling 200 consistent with the coupling 200 depicted in FIG. 2A. With reference to FIGS. 3-5 in combination with FIG. 2A, an embodiment includes an arrangement where the first orifice 206 overlaps the third orifice 210 to provide an uninterrupted straight line flow path 212, 214 through both the first and third orifices 206, 210 from the first side 202 to the second side 204, and the second orifice 208 overlaps the third orifice 210 to provide an uninterrupted straight line flow path 216, 218 through both the third and second orifices 210, 208 from the second side 204 to the first side 202. In an embodiment, the area of overlap between the first orifice 206 and the third orifice 210 is equal to 100 percent of the axial cross sectional area of the first orifice 206, and the area of overlap between the second orifice 208 and the third orifice 210 is equal to 100 percent of the axial cross sectional area of the second orifice 208, as illustrated in FIG. 5.

Figure 6:
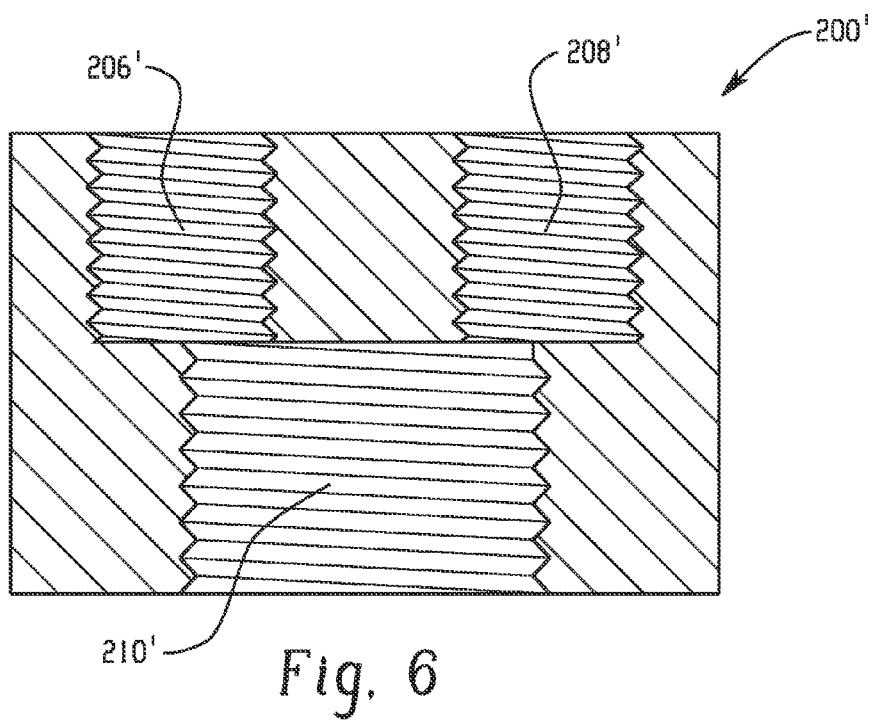
FIG. 6 depicts a cross section view of an alternative coupling, similar to the cross section view of the coupling depicted in FIG. 2A, in accordance with an embodiment of the invention.
Figure 7:
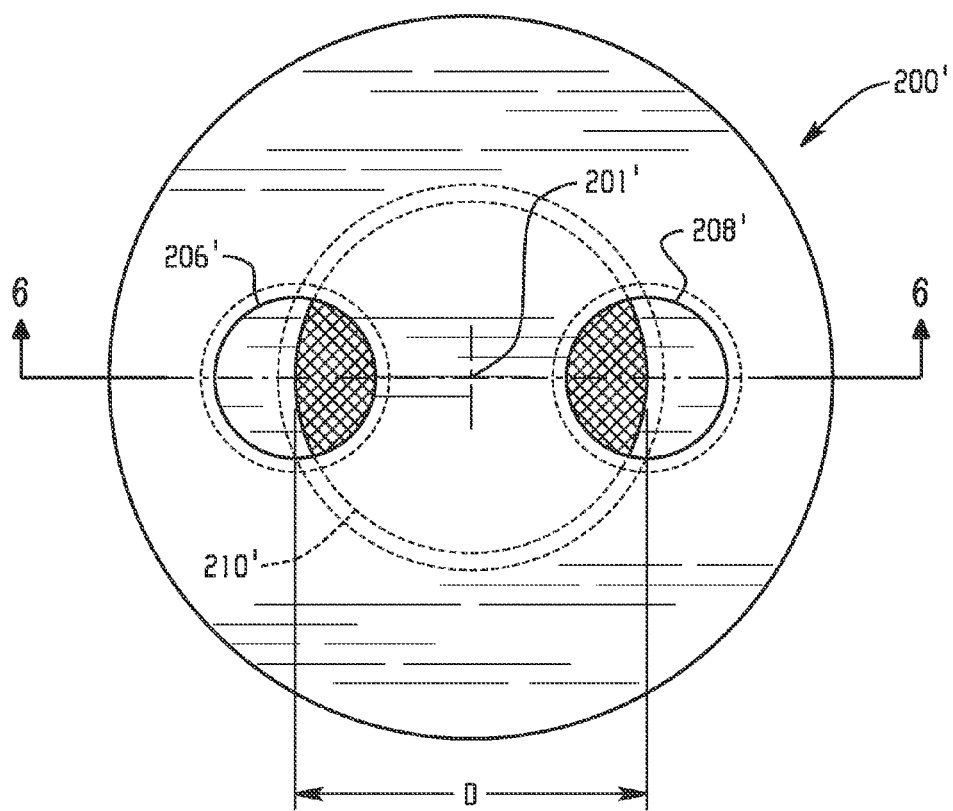
FIG. 7 depicts a top-down plan view of the alternative coupling of FIG. 6, similar to the top-down plan view of the coupling depicted in FIG. 5, in accordance with an embodiment of the invention.

While FIGS. 2-5 depict a particular coupling 200 having a particular arrangement of overlapping first, second and third orifices 206, 208, 210, that is, 100 percent overlap, it will be appreciated that the scope of the invention is not so limited, and that the scope of the invention also encompasses other degrees of overlap, which will now be discussed in connection with FIGS. 6-7, FIG. 6 depicts in cross section view an alternative coupling 200' to coupling 200, where the cross section plane is a plane that contains a central axis 201' (see FIG. 7) of the coupling 200' similar to the cross section view of the coupling 200 in FIG. 2A. Like elements between couplings 200 and 200' are referred to with like reference numerals primed. FIG. 7 depicts a top-down plan view of an embodiment of the coupling 200' consistent with the coupling 200' depicted in FIG. 6. The illustration of FIG. 7 is comparable with the illustration of FIG. 5.

As illustrated in FIGS. 6 and 7, the alternative embodiment of coupling 200' includes an arrangement where the area of overlap between the first orifice 206' and the third orifice 210' is less than 100 percent and is equal to or greater than 25 percent of the axial cross sectional area of the first orifice 206', and the area of overlap between the second orifice 208' and the third orifice 210' is less than 100 percent and is equal to or greater than 25 percent of the axial cross sectional area of the second orifice 208'. The areas of overlap between the first and third orifices 206', 210', and between the second and third orifices 208', 210', are illustrated by cross-hatching in FIG. 7. In an embodiment, the central axes of the first and second orifices 206', 208' are disposed tangent with the outer diameter D of third orifice 210'. However, other arrangements for the central axes of first and second orifices 206', 208' relative to outer diameter D are contemplated.

The third orifices 210, 210' of each coupling 200, 200', respectively, may be appropriately sized to receive the same size sample container 300, or the sample container 300 may be appropriately sized to fit different sized third orifices 210, 210'.

While certain combinations of first orifices 206, 206', second orifices 208, 208', and third orifices 210, 210', have been illustrated herein to provide a 100 percent overlap (FIGS. 2 and 5) and a greater than 25 percent overlap (FIGS. 6 and 7), it will be appreciated that these certain combinations are for illustration purposes only and that any combination of any of overlap having a range from 25 to 100 percent, relative to the third orifice 210, 210', may be employed in accordance with an embodiment of the invention disclosed herein. Any and all such combinations are contemplated herein and are considered within the scope of the invention disclosed.

It will be appreciated that the viscous consistency of pulp in an aqueous solution may lead to clogging in a sampling and/or delivery system that does not take such consistency into consideration. For example, in shut off valves that employ a compression spring in the shut off chamber, where the spring biases the valve to an open position and a turn screw is used to seat a valve seal against a valve seat to close the valve in a direction that opposes the spring bias force, the windings of the spring may create sufficient flow restriction through which water may pass but pulp may not, potentially resulting in clogging in the vicinity of the compression spring. As such, it would be advantageous to use a low-flow-restriction shut off valve to avoid such clogging, which will now be discussed in connection with FIGS. 8 and 9.

Figure 8:
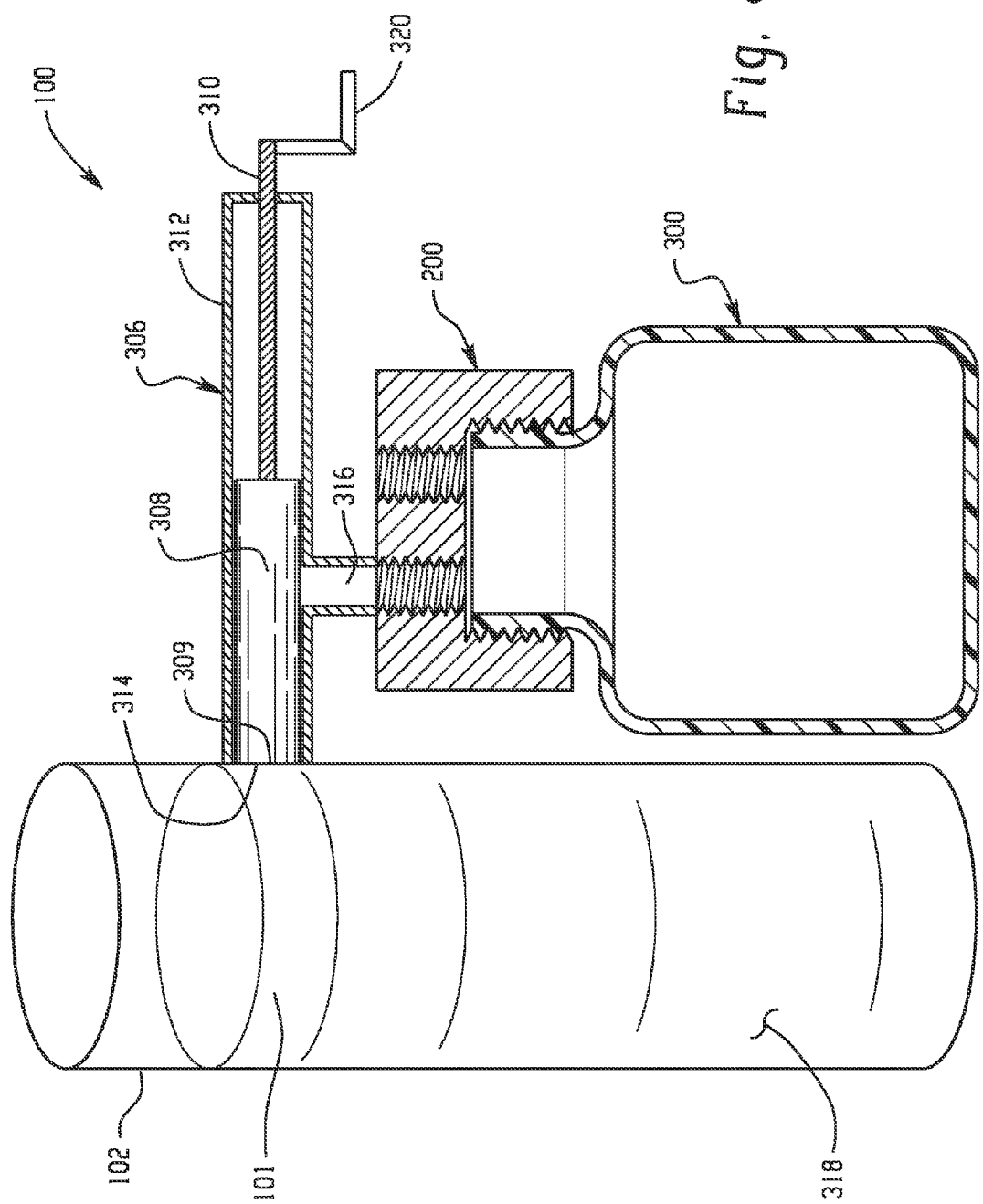
FIG. 8 depicts a system similar to that of FIG. 1, but with a low-flow-restriction shut off valve disposed in a closed position, in accordance with an embodiment of the invention.
Figure 9:
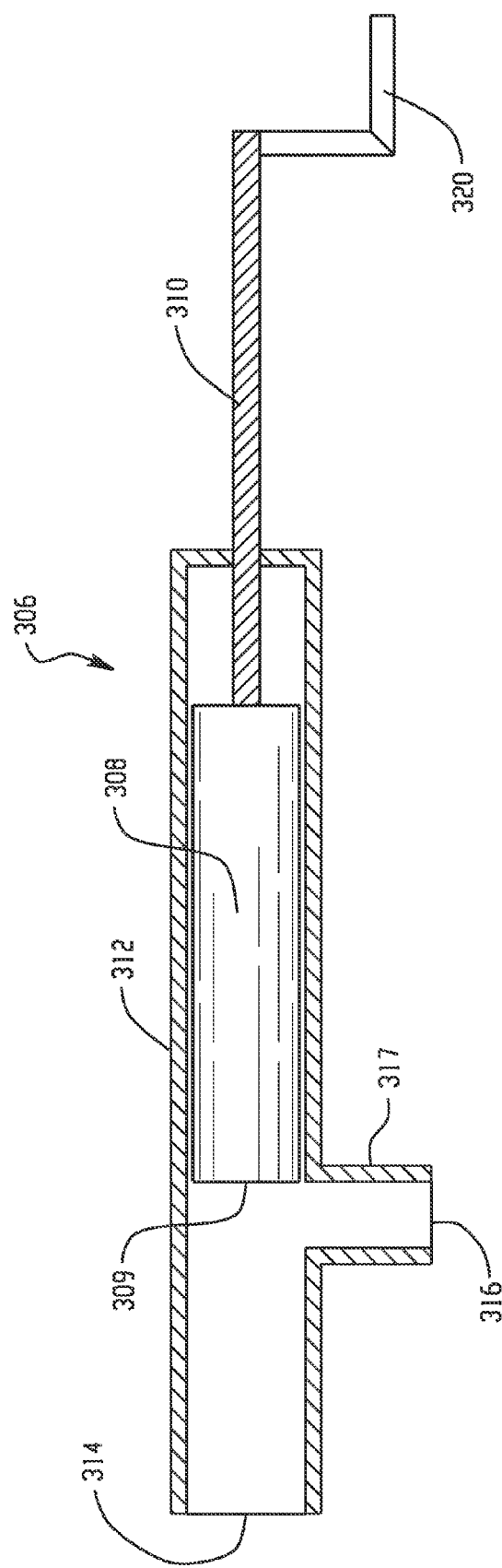
FIG. 9 depicts the low-flow-restriction shut off valve of FIG. 8 disposed in an open position, in accordance with an embodiment of the invention.

FIG. 8 depicts a system 100 similar to that of FIG. 1, but with a low-flow-restriction (LFR) shut off valve 306, and where like elements are numbered alike. In an embodiment, the LFR shut off valve 306 includes a piston 308 attached to a ball screw 310. The piston 308 operates within a housing 312 having an inlet port 314 and an outlet port 316. FIG. 8 depicts the piston 308 disposed in a closed position, where the left end 309 of the piston 308 is disposed proximate a surface of the container or conduit 318 holding the pressurized fluid source 102. FIG. 9 depicts the piston 308 disposed in an open position, where the left end 309 of the piston 308 is disposed to the right side 317 of the outlet port 316 to fully expose the outlet port 316 to provide unrestricted flow of the flowable stock 101 (FIG. 8) from the inlet port 314 to the outlet port 316.

When operating the LFR shut valve 306 from the open position to the closed position, an actuator 320 is used to turn the ball screw 310 and to drive the piston 308 not only to close off the outlet port 316, but also to push any remaining flowable stock 101 from the housing 312 out of the inlet port 314 of the LFR shut off valve 306, thereby preventing any clogging of flowable stock 101 in the LFR shut off valve 306 upstream of the coupling 200 and sample container 300. In an embodiment the piston 308 is driven to the inner surface of the container or conduit 318 holding the pressurized fluid source 102. An example of a commercially available LFR shut off valve suitable for a purpose disclosed herein can be found in Strahman's line of sampling valves available at Beaver Contromatic.

While an embodiment of LFR shut off valve 306 has been described having a ball screw 310 and mechanical actuator 320 for moving the piston 308 to either the closed position depicted in FIG. 8 or the open position depicted in FIG. 9, it will be appreciated that shut off valves having other actuation means may be employed, such as a pneumatically controlled shut off valve, or a solenoid controlled shut off valve, for example. An example of a pneumatically controlled shut off valve suitable for a purpose disclosed herein is the MCS-1000 Medium Consistency Sampling Valve available from BTG Instruments. It is contemplated that a solenoid controlled actuator can be readily substituted for a pneumatically controlled actuator to provide a sampling valve suitable for a purpose disclosed herein.

From the foregoing discussion relating to clogging, it will be appreciated that a quick acting shut valve would be advantageous over a slow acting shut valve to avoid clogging in the delivery and/or sampling system. Quick acting shut off valves suitable for a purpose disclosed herein include the aforementioned Strahman's line of sampling valves available from Beaver Contromatic, and the medium consistency sampling valves available from BTG Instruments.

While the invention has been described with reference to example embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best or only mode contemplated for carrying out this invention, but that the invention will include all embodiments falling within the scope of the appended claims. Also, in the drawings and the description, there have been disclosed example embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A combination, comprising:
    a container; and
    a coupling configured to receive the container;
    wherein the coupling comprises a unitary body having a first side and an opposing second side, the first side comprising a first orifice and a second orifice, the second side comprising a third orifice;
    wherein the first orifice is disposed in flow-through communication with the third orifice from the first side to the second side, and the third orifice is disposed in flow-through communication with the second orifice from the second side to the first side;
    wherein a first flow path through the first orifice is disposed parallel with a second flow path through the third orifice, and a third flow path through the third orifice is disposed parallel with a fourth flow path through the second orifice, and
    wherein the first orifice, the second orifice, and the third orifice, each comprise a threaded inner surface.

2. The combination of claim 1, wherein:
    the first flow path through the first orifice is disposed parallel with the fourth flow path through the second orifice.

3. The combination of claim 1, wherein:
    the first flow path through the first orifice is disposed in a straight line arrangement with the second flow path through the third orifice, and the third flow path through the third orifice is disposed in a straight line arrangement with the fourth flow path through the second orifice.

4. The combination of claim 1, wherein:
    the first flow path through the first orifice adjoins the second flow path through the third orifice, and the third flow path through the third orifice adjoins the fourth flow path through the second orifice.

5. The combination of claim 1, wherein:
    the first flow path through the first orifice adjoins the second flow path through the third orifice in a continuous uninterrupted manner, and the third flow path through the third orifice adjoins the fourth flow path through the second orifice in a continuous uninterrupted manner.

6. The combination of claim 1, wherein:
    the first orifice overlaps the third orifice to provide an uninterrupted straight line flow path through both the first and third orifices from the first side to the second side; and
    the second orifice overlaps the third orifice to provide an uninterrupted straight line flow path through both the third and second orifices from the second side to the first side.

7. The combination of claim 6, wherein:
    an area of overlap between the first orifice and the third orifice is equal to or greater than 25 percent; and
    an area of overlap between the second orifice and the third orifice is equal to or greater than 25 percent.

8. The combination of claim 1, wherein:
    the unitary body comprises material having seamless continuity from the first side to the second side.

9. The combination of claim 1, wherein:
    the container comprises a neck having threads, the threads of the third orifice being configured to threadably receive the threads of the neck of the container.

10. The combination of claim 1, wherein:
each of the threads of the first and second orifices are NPT tapered threads.

11. A coupling, comprising:
a unitary body having a first side and an opposing second side, the first side comprising a first orifice and a second orifice, the second side comprising a third orifice;
wherein the first orifice is disposed in flow-through communication with the third orifice from the first side to the second side, and the third orifice is disposed in flow-through communication with the second orifice from the second side to the first side;
wherein a first flow path through the first orifice is disposed parallel with a second flow path through the third orifice, and a third flow path through the third orifice is disposed parallel with a fourth flow path through the second orifice, and
wherein the first orifice, the second orifice, and the third orifice, each comprise a threaded inner surface.

12. The coupling of claim 11, wherein:
the first orifice overlaps the third orifice to provide an uninterrupted straight line flow path through both the first and third orifices from the first side to the second side; and
the second orifice overlaps the third orifice to provide an uninterrupted straight line flow path through both the third and second orifices from the second side to the first side.

13. The coupling of claim 12, wherein:
an area of overlap between the first orifice and the third orifice is equal to or greater than 25 percent; and
an area of overlap between the second orifice and the third orifice is equal to or greater than 25 percent.

14. The coupling of claim 11, wherein:
each of the threads of the first and second orifices are NPT tapered threads.

15. A combination, comprising:
a shut off valve; and
a coupling configured to receive the shut off valve;
wherein the coupling comprises a unitary body having a first side and an opposing second side, the first side comprising a first orifice and a second orifice, the second side comprising a third orifice;
wherein the first orifice is disposed in flow-through communication with the third orifice from the first side to the second side, and the third orifice is disposed in flow-through communication with the second orifice from the second side to the first side;
wherein a first flow path through the first orifice is disposed parallel with a second flow path through the third orifice, and a third flow path through the third orifice is disposed parallel with a fourth flow path through the second orifice, and
wherein the first orifice, the second orifice, and the third orifice, each comprise a threaded inner surface.

16. The combination of claim 15, wherein the shut off valve comprises:
a housing having an inlet port and an outlet port;
a piston actuatable within the housing to prevent flow communication from the inlet port to the outlet port when in a closed position, and to allow flow communication from the inlet port to the outlet port when in an open position;
wherein when the piston is in the closed position, a first end of the piston is disposed proximate the inlet port, and wherein when the piston is in the open position, the first end of the piston is disposed to fully expose the outlet port; and
wherein the outlet port of the shut off valve is configured to be detachably coupled to the first orifice of the coupling.

17. A combination, comprising:
a shut off valve;
a container; and
a coupling configured to receive both the shut off valve and the container;
wherein the coupling comprises a unitary body having a first side and an opposing second side, the first side comprising a first orifice and a second orifice, the second side comprising a third orifice;
wherein the first orifice is disposed in flow-through communication with the third orifice from the first side to the second side, and the third orifice is disposed in flow-through communication with the second orifice from the second side to the first side;
wherein a first flow path through the first orifice is disposed parallel with a second flow path through the third orifice, and a third flow path through the third orifice is disposed parallel with a fourth flow path through the second orifice, and
wherein the first orifice, the second orifice, and the third orifice, each comprise a threaded inner surface.

18. The combination of claim 17, wherein the shut off valve comprises:
a housing having an inlet port and an outlet port;
a piston actuatable within the housing to prevent flow communication from the inlet port to the outlet port when in a closed position, and to allow flow communication from the inlet port to the outlet port when in an open position;
wherein when the piston is in the closed position, a first end of the piston is disposed proximate the inlet port, and wherein when the piston is in the open position, the first end of the piston is disposed to fully expose the outlet port;
wherein the outlet port of the shut off valve is configured to be detachably coupled to the first orifice of the coupling; and
wherein the container is configured to be detachably coupled to the third orifice of the coupling.

* * * * *